(12) United States Patent
Tuinstra et al.

(10) Patent No.: US 9,617,530 B2
(45) Date of Patent: *Apr. 11, 2017

(54) ACETYL-CoA CARBOXYLASE HERBICIDE RESISTANT SORGHUM

(75) Inventors: Mitchell R. Tuinstra, West Lafayette, IN (US); Kassim Al-Khatib, Manhattan, KS (US)

(73) Assignee: Kansas State University Research Foundation, Inc., Manhattan, KS (US)

( * ) Notice: Subject to any disclaimer, the term of this patent is extended or adjusted under 35 U.S.C. 154(b) by 688 days.

This patent is subject to a terminal disclaimer.

(21) Appl. No.: 12/013,142

(22) Filed: Jan. 11, 2008

(65) Prior Publication Data
US 2010/0293628 A1 Nov. 18, 2010

Related U.S. Application Data

(60) Provisional application No. 60/880,125, filed on Jan. 12, 2007.

(51) Int. Cl.
*C12N 15/82* (2006.01)
*C12N 9/88* (2006.01)
*A01H 5/10* (2006.01)

(52) U.S. Cl.
CPC .................. *C12N 9/88* (2013.01); *A01H 5/10* (2013.01); *C12N 15/8274* (2013.01)

(58) Field of Classification Search
CPC .............................. C12N 9/93; C23N 15/8274
See application file for complete search history.

(56) References Cited

U.S. PATENT DOCUMENTS 5,498,544 A 3/1996 Gengenbach et al.
6,069,298 A * 5/2000 Gengenbach et al. ........ 800/278

FOREIGN PATENT DOCUMENTS

GB 2326163 12/1998
WO WO 91/03157 * 3/1991
WO WO 2008/089061 7/2008

OTHER PUBLICATIONS

Delye et al 2005, Weed Research 45: 323-330.*
Obermeier, M.R. 1998 Doctoral Dissertation, The Graduate School of the University of Kentucky, Lexington Kentucky.*
Casa et al 2005, Theoretical and Applied Genetics 111: 23-30.*
Rendina et al., Inhibition of acetyl-coenzyme . . . grass-selective herbicides. J Agric Food Chem 38: 1282-1287, 1990.
Herbert et al., Kinetic studies on two isoforms of acetyl-CoA carboxylase from maize leaves, Biochem. J. 318:997-1006, 1996.
Zhang et al., A possible point mutation . . . resistance to sethoxydim in green foxtail (*Setaria viridis*) (abstract No. 81). Weed Sci Soc Am 40: 33, 2000.
Zagnitko et al., An isoleucine/leucine . . . inhibitors, Proc Natl Acad Sci U S A. Jun. 5, 2001;98(12):6617-22. Epub May 29, 2001.
Deyle et al., SNP markers for black-grass (*Alopecurus myosuroides* Huds.) . . . , Theor. Appl. Genet. 104:1114-1120, 2002.
Deyle et al., PCR-based detection of resistance to acetyl-CoA carboxylase-inhibiting herbicides in black-grass . . . , Pest Management Science 58, 474-478, 2002.
Deyle et al., An isoleucine-leucine substitution in chloroplastic acetyl-CoA . . . herbicide sethoxydim. Planta 214, 421-427, 2002.
Christoffers et al., An Isoleucine to Leucine Mutation in Acetyl-CoA Carboxylase Confers Herbicide . . . Wild Oat, Genome 45 :1049-1056, 2002.
Nikolau et al., Plant Biotin-Containing Carboxylases, Archives of Biochemistry and Biophysics, vol. 414, No. 2, pp. 211-222, Jun. 15, 2003.
Deyle et al., Molecular Bases for Sensitivity to Acetyl-Coenzyme A Carboxylase Inhibitors in Black-Grass1, Plant Phys. 137:794-806, 2005.
Girijashankar V, et at., Development of transgenic sorghum for insect resistance against the spotted stem borer (*Chilo partellus*) Plant Cell, Rep 24, 513-522. 2005.
Delye C, et al., Universal Primers for PCR-Sequencing of Grass Chloroplastic . . . , Weed Res., 45:323-330, 2005.
Bradley, K.W., et al., "Identification of a johnsongrass (*Sorghum halepense*) biotype resistant to aryloxyphenoxypropionate . . . ", Weed Technol., vol. 15, pp. 623-627 (2001).
Bradley, K.W., et al., "The mechanism of resistance to aryloxyphenoxypropionate and cyclohexanedione herbicides in a johnsongrass . . . ", Weed Sci., vol. 49, pp. 477-484 (2001).
Brown, A.C., et al., "An isoleucine to leucine substitution in the ACCase of alopecurus myosuroides (black-grass) . . . ", Pestic. Biochem. Physiol., vol. 72, pp. 160-168 (2002).
Burke, I.C., et al., "Cross-resistance of a johnsongrass (*Sorghum halepense*) biotype to aryloxyphenoxypropionate . . . ", Weed Technol., vol. 20, pp. 571-575 (2006).
Burke, I.C., et al., "Mechanism of resistance to clethodim in a johnsongrass (*Sorghum halepense*) biotype", Weed Sci., vol. 54, pp. 401-406 (2006).
Cronan, J.E., et al., "Multi-subunit acetyl-CoA carboxylases", Prog. Lipid Res., vol. 41, pp. 407-435 (2002).
Delye, C., "Weed resistance to acetyl coenzyme A carboxylase inhibitors: An update", Weed Sci., vol. 53, pp. 728-746 (2005).
Delye, C., et al., "Nucleotide variability at the acetyl coenzyme A carboxylase gene and the signature of herbicide . . . ", Mol. Biol. Evol., vol. 21, pp. 884-892 (2004).
Delye, C., et al., "An isoleucine residue within the carboxyl-transferase domain of multidomain acetyl-coenzyme A carboxy . . . ", Plant Physiol., vol. 132, pp. 1716-1723 (2003).
Egli, M.A., et al., "Characterization of maize acetyl-coenzyme-a carboxylase", Plant Physiol., vol. 101, pp. 499-506 (1993).
Hofer, U., et al., "Pinoxaden—for broad spectrum grass weed management in cereal crops", J. Plant Dis. Prot., pp. 989-995 (2006).
Kunst, L., et al., "Biosynthesis and secretion of plant cuticular wax", Prog. Lipid Res., vol. 42, pp. 51-80 (2003).

(Continued)

*Primary Examiner* — David H Kruse

(57) ABSTRACT

The present invention provides for compositions and methods for producing crop plants that are resistant to herbicides. In particular, the present invention provides for *sorghum* plants, plant tissues and plant seeds that contain altered acetyl-CoA carboxylase (ACC) genes and proteins that are resistant to inhibition by herbicides that normally inhibit the activity of the ACC protein.

3 Claims, 1 Drawing Sheet

(56) References Cited

OTHER PUBLICATIONS

Marshall, L.C., et al., "Allelic mutations in acetyl-coenzyme a carboxylase confer herbicide tolerance in maize", Theor. Appl. Genet., vol. 83, pp. 435-442 (1992).
Miller, F.R., "Registration of Rtx430 sorghum parental line", Crop Sci., vol. 24, pp. 1224-1224 (1984).
Parker, W.B., et al., "Dominant mutations causing alterations in acetyl-coenzyme-a carboxylase confer tolerance . . . ", Proc. Natl. Acad. Sci. USA, vol. 87, pp. 7175-7179 (1990).
Podkowinski, J., et al., "Structure of a gene encoding a cytosolic acetyl-CoA carboxylase of hexaploid wheat", Proc. Natl. Acad. Sci. USA, vol. 93. pp. 1870-1874 (1996).
Secor, J., et al., "Inhibition of acetyl-coa carboxylase activity by haloxyfop and tralkoxydim", Plant Physiol., vol. 86, pp. 10-12 (1988).
Smeda, R.J., et al., "Identification of graminicide-resistant johnsongrass (Sorghum halepense)", Weed Sci., vol. 45, pp. 132-137 (1997).
Smeda, R.J., et al., "Fluazifop-P resistance expressed as a dominant trait in sorghum (Sorghum bicolor)", Weed Technol., vol. 14, pp. 397-401 (2000).
Tal, A., et al,, "Molecular characterization and inheritance of resistance to ACCase-inhibiting herbicides in lolium rigidum", Pest Manag. Sci., vol. 60, pp. 1013-1018 (2004).
Tardif, F.J., et al., "Occurrence of a herbicide-resistant acetyl-coenzyme-a carboxylase mutant in annual ryegrass . . . ", Planta, vol. 190, pp. 176-181 (1993).
White, G.M., et al., "Differences in the molecular basis of resistance to the cyclohexanedione herbicide sethoxydim in lolium . . . ", Weed Res., vol. 45, pp. 440-448 (2005).
Zhang, X.Q., et al., "Six amino acid substitutions in the carboxyltransferase domain of the plastidic acetyl-CoA . . . ", New Phytol., vol. 172, pp. 636-645 (2006).
Cummins, Ian, et al., "A role for glutathione transferases functioning as glutathione peroxidases in resistance . . . ", The Plant Journal, 18(3), 285-292 (1999).
Hall, L.M., et al., "Mechanisms of Resistance to Aryloxyphenoxypropionate Herbicides . . . ", Pesticide Biochemistry and Physiology 57, 87-98 (1997).
Accase Inhibitors (A/1) Resistant Weeds, see http://www.weedscience.org/Summary/UspeciesMOA.asp?1stMOAID=2, Copyright 1993-2011 Weedscience.org, Dec. 2011.
Delye et al., "Universal primer for PCR-sequencing of grass chloroplastic acetyl-CoA carboylase domains involved in resistance to herbicides", Weed Research, vol. 45, pp. 323-330 (2005).
Egli et al., "A Maize Acetyl-Coenzyme A Carboxylase cDNA Sequence", Plant Physiology, vol. 108, pp. 1299-1300 (1995).
Zhu et al., "Engineering herbicide-resistant maize using chimeric RNA/DNA oligonucleotides", Nature Biotechnology vol. 18, pp. 555-558 (2000).
International Search Report, International Application No. PCT/US2008/50856, mailed Oct. 29, 2008.
Maneechote et al., "Resistant Acetyl-CoA Carboxylase is a Mechanism of Herbicide Resistance in a Biotype of *Avena sterilis* ssp. *ludoviciana*", Plant Cell Physiol. 35(4):627-635 (1994).
Tardiff et al., "Resistance to Acetyl-Coenzyme A Carboxylase-Inhibiting Herbicides Endowed by a Single Major Gene Encoding a Resistance Target Site in a Biotype of Lolium rigidum," Australian J. Plant Physiol. 23(1):15-23 (1996).
Sasaki and Nagano, "Plant acetyl-CoA carboxylase: structure, biosynthesis, regulation, and gene manipulation for plant breeding", Biosci. Biotechnol. Biochem. 68:1175-1184 (2004).
Mary Joy Abit, Grain Sorghum Response to Postemergence Applications of Mesotrione and Quizalofop, Ph.D. Dissertation, Kansas State University (2010).
Kellen S. Kershner, "Herbicide Resistance in Grain Sorghum", Ph.D. Dissertation, Kansas State University (2010).

\* cited by examiner

```
           980              990             1000            1010
Bol-71: ACC herbicide tolerant        GGCTAACTGCAGAGGTTTCTCTGGTGGACAGAGAGATCTCT
R91: ACC herbicide tolerant           GGCTAACTGCAGAGGTTTCTCTGGTGGACAGAGAGATCTCT
Bol-36: ACC herbicide susceptible     GGCTAACTGGAGAGGTTTCTCTGGTGGACAGAGAGATCTCT
ATx623: ACC herbicide susceptible     GGCTAACTGGAGAGGTTTCTCTGGTGGACAGAGAGATCTCT Tx430: ACC herbicide susceptible      GGCTAACTGGAGAGGTTTCTCTGGTGGACAGAGAGATCTCT
Bol-36: ACC herbicide susceptible     GGCTAACTGCAGAGGTTTCTCTGGTGGACAGAGAGATCTCT
R91: ACC herbicide susceptible        GGCTAACTGCAGAGGTTTCTCTGGTGGACAGAGAGATCTCT
Bol-71: ACC herbicide tolerant        GGCTAACTGCAGAGGTTTCTCTGGTGGACAGAGAGATCTCT
R91: ACC herbicide tolerant           GGCTAACTGGAGAGGTTTCTCTGGTGGACAGAGAGATCTCT
ATx623: ACC herbicide susceptible     GGCTAACTG AGAGGTTTCTCTGGTGGACAGAGAGATCTCT
```

ACETYL-COA CARBOXYLASE HERBICIDE RESISTANT SORGHUM

The present application claims priority to U.S. Provisional Application No. 60/880,125 filed Jan. 12, 2007, incorporated herein by reference in its entirety.

FIELD OF THE INVENTION

The present invention provides for compositions and methods for producing crop plants that are resistant to herbicides. In particular, the present invention provides for *sorghum* plants, plant tissues and plant seeds that contain altered acetyl-CoA carboxylase (ACC) genes and proteins that are resistant to inhibition by herbicides that normally inhibit the activity of the ACC protein.

BACKGROUND OF THE INVENTION

*Sorghum* is the second most important cereal-feed grain grown in the United States. Production is economically critical to farms operating in marginal rainfall areas because of *sorghum*'s ability to tolerate drought and heat. Both the livestock and bio-energy industries utilize *sorghum* as an energy substrate thereby making it a versatile crop.

Worldwide, *sorghum* is the fifth leading cereal grain. As it is tolerant to both drought and heat, it is easily the most widely grown food grain in the semiarid regions of sub-Sahelian Africa and in the dry central peninsular region of India. As such, *sorghum* is used in human consumption in most of the driest regions of the world thereby making it a critically important food crop in these locations.

The development of herbicide resistance in plants offers significant production and economic advantages; as such the use of herbicides for controlling weeds or plants in crops has become almost a universal practice. However, application of such herbicides can also result in death or reduced growth of the desired crop plant, making the time and method of herbicide application critical or in some cases unfeasible.

Of particular interest to farmers is the use of herbicides with greater potency, broad weed spectrum effectiveness and rapid soil degradation. Plants, plant tissues and seeds with resistance to these compounds would provide an attractive solution by allowing the herbicides to be used to control weed growth, without risk of damage to the crop. One such class of broad spectrum herbicides are those compounds that inhibit the activity of the acetyl-CoA carboxylase (ACC) enzyme in a plant. Such herbicides are included in the aryloxyphenoxypropionate (FOP) and cyclohexanedione (DIM) chemical families. For example, *sorghum* is susceptible to many ACC inhibiting herbicides that target monocot species, making the use of these herbicides to control grassy weeds almost impossible.

Certain weed grass species have been found that display altered sensitivity to FOP and DIM herbicides. One grass species, black grass (*A. myosuroides* [Huds.]), is a major grass weed in Europe. Several mutations have been found in the genome of some black grass plants that confer resistance to some, but not all, FOP and DIM herbicides (Délve, et al., 2005, Plant Phys. 137:794-806; Délye, et al., 2002, Theor. Appl. Genet. 104:1114-1120). Similar findings were found in mutant grass weeds such as annual ryegrass (*L. rigidum* [Gaud.]; Délye, et al., 2002, Pest Manag. Sci. 58:474-478), green foxtail (*S. viridis* [L. Beauv.]; Zhang and Devine, 2000, Weed Sci. Soc. Am. 40:33; Délye, et al., 2002, Planta 214:421-427) and wild oat (*A. fatua* [L.]; Christoffers et al., 2002, Genome 45:1049-1056). One herbicide resistant maize hybrid (DK592 from Dekalb) has a similar mutation in the ACC enzyme as that found in grass weeds (Zagnitko et al., 2001, Proc. Natl. Acad. Sci. 98:6617-22).

Due to the importance of *sorghum* as a crop plant on the world stage, what are needed are *sorghum* hybrids that are resistant to the inhibitory effects of ACC herbicides, thereby allowing for greater crop yield when these herbicides are used to control grassy weeds.

SUMMARY OF THE INVENTION

The present invention provides for compositions and methods for producing *sorghum* cultivars that are resistant to herbicides. In particular, the present invention provides for *sorghum* plants, plant tissues and plant seeds that contain altered acetyl-CoA carboxylase (ACC) genes and proteins that are resistant to inhibition by herbicides that normally inhibit the activity of the ACC protein.

Cultivated *sorghum* [*Sorghum bicolor* (L.) Moench] is susceptible to many ACC inhibiting herbicides that target monocot or grassy weed species. However, as described herein a *sorghum* genotype was found that exhibits tolerance to ACC inhibiting herbicides. Genetic analysis has identified genetic differences within a wild *sorghum* germplasm that results in an ACC herbicide resistance phenotype.

In one embodiment, the present invention provides for one or more *sorghum* plants whose germplasm comprises a mutation that renders the plant tolerant to ACC herbicides. Moreover, in further embodiments the invention relates to the offspring (e.g., F1, F2, F3, etc.) of a cross of said plant wherein the germplasm of said offspring has the same mutation as the parent plant. Therefore, embodiments of the present invention provide for *sorghum* hybrids whose germplasm contains a mutation, such that the phenotype of the plants is ACC herbicide resistance. In some embodiments, said offspring (e.g., F1, F2, F3, etc.) are the result of a cross between elite *sorghum* lines, at least one of which contains a germplasm comprising a mutation that renders the plant tolerant to ACC herbicides.

In one embodiment, the present invention provides a *sorghum* hybrid wherein said *sorghum* hybrid germplasm confers resistance to inhibition by one or more acetyl-CoA carboxylase herbicides at levels of said one or more herbicides that would normally inhibit the growth of a *sorghum* hybrid. In some embodiments, said one or more acetyl-CoA carboxylase herbicides are from aryloxyphenoxypropionate (FOP) and cyclohexanedione (DIM) chemical families. In some embodiments, said *sorghum* hybrid germplasm that confers resistance to inhibition by one or more acetyl-CoA carboxylase herbicides comprises one or more mutations in the acetyl-CoA carboxylase gene as found in ATCC No. PTA-8033 or as found in ATCC No. PYA-8034.

In one embodiment, the present invention provides a method of controlling weeds in the vicinity of a *sorghum* hybrid, comprising providing one or more acetyl-CoA carboxylase herbicides, applying said one or more acetyl-CoA carboxylase herbicides to a field comprising a *sorghum* hybrid, and controlling weeds in the vicinity of said *sorghum* hybrid such that weed growth is adversely affected by the application of said one or more herbicides and growth of said *sorghum* hybrid is not adversely affected. In some embodiments, said one or more acetyl-CoA carboxylase herbicides are from aryloxyphenoxypropionate (FOP) and cyclohexanedione (DIM) chemical families. In some embodiments, said *sorghum* hybrid comprises one or more mutations in the acetyl-CoA carboxylase gene as found in ATCC No. PTA-8033 or ATCC No. PYA-8034.

In one embodiment, the present invention provides a *sorghum* hybrid, wherein said *sorghum* hybrid comprises a germplasm comprising one or more mutations in the acetyl-CoA carboxylase gene such that resistance to one or more acetyl-CoA carboxylase herbicides is conferred to said hybrid. In some embodiments, said *sorghum* hybrid is created by introgression of a *sorghum* germplasm that comprises said one or more mutations for conferring resistance to one or more acetyl-CoA carboxylase herbicides. In some embodiments, said *sorghum* hybrid is created by incorporation of a heterologous gene comprising one or more mutations for conferring resistance to one or more acetyl-CoA carboxylase herbicides.

In one embodiment, the present invention provides a method for producing a *sorghum* hybrid plant line resistant to one or more acetyl-CoA carboxylase herbicides comprising identifying a germplasm conferring said herbicide resistance, wherein said herbicide resistant germplasm derives from an herbicide resistant *sorghum* plant, and introducing said germplasm into an elite *sorghum* plant line. In some embodiments, said introducing of said germplasm into said elite *sorghum* plant line is by introgression. In some embodiments, said introducing of said germplasm into said elite *sorghum* plant line is by introduction of a heterologous gene.

In one embodiment, the present invention provides a *sorghum* hybrid wherein the germplasm of said hybrid comprises conferred resistance to one or more acetyl-CoA carboxylase herbicides and resistance to one or more compounds from one or more herbicide groups that are not acetyl-CoA carboxylase inhibitors.

In one embodiment, the present invention provides a method for identifying *sorghum* plant lines resistant to acetyl-CoA carboxylase herbicides comprising supplying a nucleic acid sample from a *sorghum* plant, providing amplification primers for amplifying a region of a *sorghum* plant corresponding to an acetyl-CoA carboxylase gene present in said nucleic acid sample, applying said amplification primers to said nucleic acid sample such that amplification of said region of said acetyl-CoA carboxylase gene occurs, and identifying *sorghum* plants resistant to acetyl-CoA carboxylase herbicides based on the presence of one or more mutations that confer acetyl-CoA carboxylase herbicide resistance present in said amplified nucleic acid sample.

In one embodiment, the present invention provides for *sorghum* seeds wherein said germplasm of said seeds comprises a mutant acetyl-CoA carboxylase gene such that said mutation confers resistance to inhibition by acetyl-CoA carboxylase herbicides. In some embodiments, the germplasm of said *sorghum* seeds comprise a mutant acetyl-CoA carboxylase gene as found in ATCC No. PTA-8033 or ATCC No. PYA-8034. In some embodiments, the present invention provides for *sorghum* plants that grow from said seeds and further plant parts that comprise said *sorghum* plants grown from said seeds. In some embodiments, the mutant acetyl-CoA carboxylase gene is a functional fragment of the gene as found in ATCC No. PTA-8033 or ATCC No. PYA-8034, such that the gene fragment encodes a protein fragment that is sufficient to confer resistance to inhibition by acetyl-CoA carboxylase herbicides to a *sorghum* plant. In some embodiments, the present invention provides for *sorghum* plants that grow from said seeds and further plant parts that comprise said *sorghum* plants grown from said seeds.

In some embodiments, the present invention provides for a *sorghum* hybrid that comprises a gene that is at least 70% homologous, at least 80% homologous, at least 85% homologous, at least 90% homologous, at least 95% homologous, at least 97% homologous, or at least 99% homologous to the acetyl-CoA carboxylase gene as found in ATCC No. PTA-8033 or ATCC No. PYA-8034. In some embodiments, the acetyl-CoA carboxylase herbicide resistance gene that is as least 70% homologous, at least 80% homologous, at least 85% homologous, at least 90% homologous, at least 95% homologous, at least 97% homologous, or at least 99% homologous to SEQ ID NO: 12 as found in ATCC No. PTA-8033 and/or ATCC No. PYA-8034 comprises one or more amino acid substitutions, for example, a tryptophan to cysteine amino acid substitution at an amino acid position aligning with $Trp_{7027}$ of the *A. myosuroides* Huds. ACC protein as found in SEQ ID NO: 12.

In one embodiment, the present invention further provides for *sorghum* hybrid plants that have all the physiological and morphological characteristics of said *sorghum* plant grown from said *sorghum* seed. In further embodiments, the present invention provides for tissue cultures and regenerated tissue cultures that arise from said *sorghum* seed or said *sorghum* plant part that comprises a mutation in said acetyl-CoA carboxylase gene as found in ATCC No. PTA-8033 or ATCC No. PYA-8034.

In one embodiment, the present invention provides a method of producing *sorghum* seed comprising crossing a plant comprising a mutant acetyl-CoA carboxylase gene as found in ATCC No. PTA-8033 or ATCC No. PYA-8034 with itself or a second *sorghum* plant and collecting said seed from said cross. In some embodiments, the methods for producing said *sorghum* seed comprises planting a parent seed *sorghum* line wherein said parent seed line comprises a germplasm that confers resistance to acetyl-CoA carboxylase herbicides with a parent pollinator *sorghum* line wherein said pollinator and/or seed line germplasm comprises a germplasm that confers resistance to acetyl-CoA carboxylase herbicides, growing said parent seed and pollinator *sorghum* plants together, allowing for the said parent seed plants to be pollinated by said parent pollinator plants, and harvesting the seed that results from said pollination.

DESCRIPTION OF THE FIGURES

FIG. 1 shows the mutation of tryptophan (TGG) to cysteine (TGC) in the *sorghum* ACC gene found to be associated with ACC herbicide resistance. *Sorghum* line Bol-71 ACC gene (bases 977-1017)—SEQ ID NOs: 2 and 9. *Sorghum* line R91 ACC gene (bases 977-1017)—SEQ ID NOs: 3, 8, and 10. *Sorghum* line Bol-36 ACC gene (bases 977-1017)—SEQ ID NOs: 4 and 7. *Sorghum* line ATx623 ACC gene (bases 977-1017)—SEQ ID NOs: 5 and 11. *Sorghum* line Tx430 ACC gene (bases 977-1017)—SEQ ID NO:6.

DEFINITIONS

As used herein, the term "variety" and "cultivar" refers to plants that are defined by the expression of the characteristics resulting from a given genotype or combination of genotypes, distinguished from any other plant grouping by the expression of at least one of the characteristics and considered as a unit with regard to its suitability for being propagation unchanged.

As used herein, the term "hybrid" refers to the offspring or progeny of genetically dissimilar plant parents or stock produced as the result of controlled cross-pollination as opposed to a non-hybrid seed produced as the result of natural pollination.

As used herein, the term "progeny" refers to generations of a plant, wherein the ancestry of the generation can be traced back to said plant.

As used herein, the term "derivative" of an herbicide resistant plant includes both the progeny of that herbicide resistant plant, as well as any mutant, recombinant, or genetically engineered derivative of that plant, whether of the same species or a different species, where the herbicide resistant characteristic(s) of the original herbicide resistant plant has been transferred to the derivative plant.

As used herein, the term "plant tissue" includes differentiated and undifferentiated tissues of plants including those present in roots, shoots, leaves, pollen, seeds and tumors, as well as cells in culture (e.g., single cells, protoplasts, embryos, cellus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, and a cell. In some embodiments of the present invention transgenic plants are crop plants.

As used herein, the terms "crop" and "crop plant" are used in their broadest sense. The term includes, but is not limited to, any species of plant edible by humans or used as a feed for animal or fish or marine animal, or consumed by humans, or used by humans, or viewed by humans, or any plant used in industry or commerce or education.

As used herein, the terms "F-generation" and "filial generation" refers to any of the consecutive generations of plants, cells, tissues or organisms after a biparental cross. The generation resulting from a mating of the a biparental cross (i.e. two parents) is the first filial generation (designated as "F1" and "$F_1$") in reference to a seed and it's plant, while that resulting from crossing of F1 individual is the second filial generation (designated as "F2" or "$F_2$") in reference to a seed and it's plant. For example, an F2 seed and a resulting plant are produced by self-pollination or cross-pollination of F1, while later F generations are produced from self-pollination or cross-pollination of the immediate prior generation.

As used herein, the term "germplasm" refers to any genetic material of plants that contain functional units of heredity.

As used herein, the term "elite germplasm" in reference to a plant refers to hereditary material of proven genetic superiority.

As used herein, the term "elite plant," refers to any plant that has resulted from breeding and selection for superior agronomic performance.

As used herein, the term "trait" refers to an observable and/measurable characteristic of an organism. For example, the present invention describes plants that are resistant to FOP and DIM herbicides.

As used herein, the terms "marker" and "DNA marker" and "molecular marker" in reference to a "selectable marker" refers to a physiological or morphological trait that may be determined as a marker for its own selection or for selection of other traits closely linked to that marker. For example, such a marker could be a gene or trait that associates with herbicide tolerance including, but not limited to, simple sequence repeat (SSR), single nucleotide polymorphism (SNP), genetic insertions and/or deletions and the like.

As used herein, the term "introgress" and "introgressing" and "introgression" refers to conventional (i.e. classic) pollination breeding techniques to incorporate foreign genetic material into a line of breeding stock. For example, the present invention provides for *sorghum* crop plants introgressed with a mutant ACC gene for herbicide tolerance by crossing two plant generations.

As used herein, the term "wild-type" when made in reference to a gene refers to a functional gene common throughout a plant population. A functional wild-type gene is that which is most frequently observed in a population and is thus arbitrarily designated the "normal" or "wild-type" form of the gene.

As used herein, the terms "modified" or "mutant" or "functional mutant" when made in reference to a gene or to a gene product refers, respectively, to a gene or to a gene product which displays modifications in sequence and/or functional properties (i.e., altered characteristics) when compared to the wild-type gene or gene product. Thus, the terms "modified" and "mutant" when used in reference to a nucleotide sequence refer to an nucleic acid sequence that differs by one or more nucleotides from another, usually related nucleotide acid sequence and the term "functional mutant" when used in reference to a polypeptide encodes by said "modified" or "mutant" nucleic acid refers to the protein or polypeptide that retains activity. In the present application, the ACC mutant protein, "or functional mutant" thereof is an ACC gene that retains its native activity to create essential amino acids. Additionally, a "modified" nucleotide sequence is interpreted as that found in the degenerate genetic code as known by those skilled in the art. For example, the genetic code is degenerate as there are instances in which different codons specify the same amino acid; a genetic code in which some amino acids may each be encoded by more than one codon. It is contemplated that the present invention may comprise such degeneracy (e.g., wherein a *sorghum* hybrid comprises an ACC gene that is at least 70% homologous, at least 80% homologous, at least 85% homologous, at least 90% homologous, at least 95% homologous, at least 97% homologous, or at least 99% homologous to SEQ ID NO: 1) as found in, for example, the *sorghum* germplasm.

As used herein, the term "heterologous" when used in reference to a gene or nucleic acid refers to a gene that has been manipulated in some way.

As used herein, the term "portion" or "functional fragment" when used in reference to a protein (as in "a fragment of a given protein", "a protein fragment", a "portion of a protein") refers to fragments of that protein. The fragments may range in size from four amino acid residues to the entire amino acid sequence minus one amino acid. In the present invention, the protein fragment is preferentially functional such that the protein fragment confers resistance to inhibition to ACC herbicides to a given plant.

DETAILED DESCRIPTION OF THE INVENTION

Acetyl-CoA carboxylase (ACC) is a biotinylated enzyme that catalyzes the carboxylation of acetyl-CoA to produce malonyl-CoA. This carboxylation is a two-step, reversible reaction consisting of the ATP-dependent carboxylation of the biotin group on the carboxyl carrier domain by biotin-carboxylase activity followed by the transfer of the carboxyl group from biotin to acetyl-CoA by carboxyl-transferase activity (Nikolau et al., 2003, Arch. Biochem. Biophys. 414:211-22). Acetyl-CoA carboxylase is not only a key enzyme in plants for biosynthesis of fatty acids, a process that occurs in chloroplasts and mitochondria, but ACC also plays a role in the formation of long-chain fatty acids and flavonoids, and in malonylation that occurs in the cytoplasm.

There are two isoforms of ACC with the chloroplastic ACC accounting for more than 80% of the total ACC activity (Herbert et al., 1996, Biochem. J. 318:997-1006). Aryloxyphenoxypropionate (FOP) and cyclohexanedione (DIM) are two classes of chemicals that are known to selectively inhibit chloroplastic ACC in grasses (Rendina et al., 1990, J. Agric. Food Chem. 38:1282-1287).

Seeds from 83 wild *sorghum* populations from Bolivia were planted and evaluated for tolerance to ACC herbicides. One of the wild *sorghum* genotypes, Bol-71, expressed high levels of tolerance to each of the herbicides tested. It is demonstrated herein that crossing the Bol-71 wild *sorghum* with elite parent *sorghum* plant lines yields good seed set and ACC herbicide resistance in F1 hybrids. For example, seeds from cross Bol-71 and ATx623, designated KSU 06 GHATx623×174 (e.g., F1 progeny), were deposited at ATCC as described herein.

As such, one embodiment of the present invention provides a *sorghum* germplasm that contains altered ACC genes and proteins. In some embodiments, the present invention provides for the use of ACC herbicides in fields of hybrid *sorghum* crop plants to reduce the amount of monocot weed plants present in said crop field, wherein said hybrid *sorghum* germplasm comprises an altered ACC enzyme that confers resistance to ACC herbicides and said weed plants are ACC herbicide susceptible.

In one embodiment, the present invention provides a *sorghum* germplasm that confers resistance to inhibition by ACC herbicides, singly or in conjunction with other resistance traits, for example insect resistance against the spotted stem borer *Chilo partellus* (Girijashankar et al., 2005, Plant Cell Rep. 24:513-522, incorporated herein in its entirety). In some embodiments, for example, a *sorghum* hybrid whose germplasm comprises a synthetic cryl Ac gene from *Bacillus thuringiensis* (Bt) is introgressed into a *sorghum* line whose germplasm confers resistance to ACC herbicides. As well, the incorporation of ACC herbicide resistance and insect resistance is accomplished via plant transgenesis into the same *sorghum* hybrid. One skilled in the art will recognize the various techniques as described herein that are applicable to the incorporation of two or more resistance attributes into the same *sorghum* hybrid.

In one embodiment, the present invention provides ACC herbicide resistance in *sorghum* plants comprising, for example, an ACC germplasm designated KSU 06GH701-715bk or KSU 06GHATx623x714 deposited under ATCC accession Nos: PTA-8033 and PYA-8034, respectively, incorporated into elite *sorghum* varieties through plant breeding and selection, thereby providing for the development of herbicide tolerant *sorghum* crop hybrids that will tolerate the use of ACC inhibiting herbicides for weed control. Deployment of this herbicide tolerance trait in the aforementioned hybrids allows use of these herbicides to control monocot weeds that grow in the presence of these crops. In some embodiments, the incorporation of the ACC resistance germplasm into elite lines is via introgression, or classical breeding methods. In some embodiments, the incorporation of the ACC resistance gene into elite lines is via heterologous gene transgenesis. In some embodiments, the invention provides a *sorghum* hybrid, wherein at least one ancestor of the *sorghum* hybrid comprises an ACC resistant gene from germplasm designated KSU 06GH701-715bk or KSU 06GHATx623x714 deposited under ATCC accession Nos: PTA-8033 and PYA-8034, respectively. In some embodiments, the ACC resistant herbicide gene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714. In some embodiments, the ACC resistant herbicide gene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714 comprising a tryptophan to cysteine amino acid substitution at an amino acid position aligning with $Trp_{2027}$ of the *A. myosuroides* Huds. ACC protein.

In some embodiments, ACC herbicide resistant germplasm is introgressed into an elite *sorghum* line using classic breeding techniques. Examples of classical breeding methods for *sorghum* can be found in, for example, Sleper and Poehlman, 2006, Breeding Field Crops, Fifth Edition, Blackwell Publishing, incorporated herein in its entirety.

In one embodiment, the ACC herbicide resistant germplasm is introgressed into a *sorghum* plant that provides food for human consumption. In some embodiments, the ACC herbicide resistant germplasm is introgressed into *sorghum* plants that provide food for livestock (e.g., poultry, cattle, swine, sheep, etc). In some embodiments, the ACC herbicide resistant germplasm is introgressed into *sorghum* plants that are used in industrial processes such as ethanol production. In one embodiment, the ACC herbicide resistant gene is introduced into the plant genome via transgenesis using vectors and technologies known in the art.

In some embodiments, the present invention provides an ACC resistant germplasm of a *sorghum* plant part of line Bol-71 and Atx623, wherein seed of said *sorghum* plant having been deposited under ATCC accession Nos: PTA-8033 and PYA-8034, respectively, and said *sorghum* plant part is one or more of a pollen, an ovule, a tissue, a pod, a seed, and a cell. In one embodiment, the present invention provides an F1 hybrid whose germplasm comprises an ACC resistance gene as described herein. In some embodiments, the F1 hybrid is a cross between two elite *sorghum* lines, at least one of which contains a germplasm comprising an ACC resistance gene as described herein.

In one embodiment, the present invention provides methods for controlling weeds in a field of hybrid *sorghum* crop plants. In some embodiments, controlling the weeds comprises applying an ACC herbicide to said field of *sorghum* plants, such that weed growth is inhibited but *sorghum* growth is not adversely affected. In some embodiments, the ACC herbicide being applied is from the aryloxyphenoxypropionate (FOP) herbicide family including, but not limited to, clodinafop-propargyl, cyhalofop-butyl, diclofop-methyl, fenoxaprop-p-ethyl, fluazifop-b-butyl, haloxyfop-ethoxyethyl, haloxyfop-etotyl, haloxyfop-R-methyl, propaquizafop, quizalofop-p-ethyl and quizalo-P-refuryl compounds. In some embodiments, the ACC herbicide being applied is from the cyclohexanediones (DIM) herbicide family including, but not limited to, alloxydim, butroxydim, clefoxydim, clethodim, cycloxydim, profoxydim, sethoxydim, tepraloxydim and tralkoxydim compounds. In some embodiments, the ACC herbicide being applied comprises a combination of compounds from both FOP and DIM ACC herbicide families as disclosed herein. However, the present application is not limited to the ACC herbicide used, and a skilled artisan will appreciate that new ACC herbicides are being discovered at any given time that inhibit the ACC enzyme.

In one embodiment, the present invention provides for a *sorghum* hybrid (e.g., F1, F2, F3, F4, etc.) whose germplasm confers resistance to ACC herbicides and resistance to one or more additional herbicides from one or more different herbicide groups. For example, additional herbicide groups used to inhibit weed growth, include, but are not limited to, inhibitors of lipid synthesis (e.g., aryloxyphenoxypropionates, cyclohexanodeiones, benzofuranes, chloro-carbonic acids, phosphorodithioates, thiocarbamates), inhibitors of photosynthesis at photosystem II (e.g., phenyl-carbamates, pyridazinones, triazines, triazinones, triazolinones, uracils, amides, ureas, benzothiadiazinones, nitriles, phenyl-pyridines), inhibitors of photosynthesis at photosystem I (e.g., bipyridyliums), inhibitors of protoporphyrinogen oxidase (e.g., diphenylethers, N-phenylphthalimides, oxadiazoles, oxyzolidinediones, phenylpyrazoles, pyrimidindiones, thiadiazoles), inhibitors of carotenoid biosynthesis (e.g., pyridazinones, pyridinecarboxamides, isoxazolidinones, triazoles), inhibitors of 4-hydroxyphenyl-pyruvate-dioxygenase (e.g., callistemones, isoxazoles, pyrazoles, triketones), inhibitors of EPSP synthase (e.g., glycines), inhibitors of glutamine synthetase (e.g., phosphinic acids), inhibitors of dihydropteroate synthase (e.g., carbamates), inhibitors of microtubule assembly (e.g., benzamides, benzoic acids, dinitroanilines, phosphoroamidates, pyridines), inhibitors of cell division (e.g., acetamides, chloroacetamides, oxyacetamides), inhibitors of cell wall synthesis (e.g., nitriles, triazolocarboxamides) and inhibitors of auxin transport (e.g., phthalamates, semicarbazones). In some embodiments, the present invention provides F1 hybrids from elite *sorghum* lines that comprises resistance to one or more ACC herbicides alone, or in conjunction with, herbicide resistance to one or more of the aforementioned herbicide groups.

In one embodiment, the present invention provides use of a transgene comprising a heterologous gene such as a gene encoding a mutant ACC protein for providing the selected agronomic trait of ACC herbicide resistance. In one embodiment, the transgene comprises a mutant ACC gene as found in the germplasm designated KSU 06GH701-715bk or KSU 06GHATx623x714 deposited under ATCC accession Nos: PTA-8033 and PYA-8034, respectively. In some embodiments, the transgene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714 (e.g., SEQ ID NO: 12). In some embodiments, the ACC resistant herbicide gene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714 comprising a tryptophan to cysteine amino acid substitution at an amino acid position aligning with $Trp_{7027}$ of the *A. myosuroides* Huds. ACC protein.

Classical Breeding of *Sorghum*

Field crops have been classically bred through techniques that take advantage of the plants method(s) of pollination. A plant is considered "self-pollinating" if pollen from one flower can be transmitted to the same or another flower, whereas plants are considered "cross-pollinated" if the pollen has to come from a flower on a different plant in order for pollination to occur.

Plants that are self-pollinated and selected over many generations become homozygous at most, if not all, of their gene loci, thereby producing a uniform population of true breeding progeny. A cross between two homozygous plants from differing backgrounds or two different homozygous lines will produce a uniform population of hybrid plants that will more than likely be heterozygous at a number of the gene loci. A cross of two plants that are each heterozygous at a number of gene loci will produce a generation of hybrid plants that are genetically different and are not uniform.

*Sorghum* plants are self-pollinating plants, but they can also be bred by cross-pollination. The development of *sorghum* hybrids requires the development of pollinator parents (fertility restorers) and seed parent inbreds using the cytoplasmic male sterility-fertility restorer system, the crossing of seed parents and pollinator parents, and the evaluation of the crosses. Pedigree breeding programs combine desirable traits; in the present application the desirable trait being plant resistance to ACC herbicides. This trait is put into the breeding pool from one or more lines, such that new inbred lines are created by crossing, followed by selection of plants with the desired trait, followed by more crossing, etc. New inbreds are crossed with other inbred lines (e.g., elite plant lines like those described herein).

Pedigree breeding starts with the crossing of two genotypes, such as Bol-71 and an elite *sorghum* line (e.g., Tx430, 00MN7645, BTx623, ATx623, Wheatland, Tx3042, OK11, QL41 and Tx643, Tx2737, Tx2783, and HP162). For example, Bol-71 wild *sorghum* parent was crossed to elite *sorghum* parent lines including Tx430, 00MN7645, BTx623 and ATx623. If the original two parents do not provide all of the desired characteristics, then other sources can be included in the breeding population. For example, if a hybrid is desired such that both ACC herbicide resistance and resistance to another herbicide group as described herein was desirous, then plants with both these attributes could be crossed using classical breeding techniques. In the pedigree method, superior plants are selfed and selected in successive generations. In the succeeding generations, the heterozygous condition gives way to homogeneous lines as a result of self-pollination and selection. Typically, in the pedigree method, five or more generations of selfing and selection are practiced (e.g., S1, S2, S3, S4, S5, etc.).

Backcrossing is used to improve a plant line. Backcrossing transfers a specific desirable trait from one source to another that lacks the trait. This is accomplished by, for example, crossing a donor (e.g., Bol-71) to an inbred line (e.g., an elite line as described herein). The progeny of this cross is then crossed back (i.e. backcrossing) to the elite inbred line, followed by selection in the resultant progeny for the desired trait (e.g., resistance to ACC herbicides). Following five or more backcross generations with selection for the desired trait the progeny are typically heterozygous for the locus (loci) controlling the desired phenotype, but will be like the elite parent for the other genetic traits. The last backcrossing then is typically selfed in order to give a pure breeding progeny for the gene being transferred.

In current hybrid *sorghum* breeding programs, new parent lines are developed to be either seed-parent lines (e.g., Wheatland, Tx3042, OK11, QL41 and Tx643) or pollen-parent lines (e.g., Tx430, Tx2737, Tx2783, 00MN7645 and HP162) depending on whether or not they contain fertility restoring genes; the seed-parent lines do not have fertility restoring genes and are male-sterile in certain cytoplasms (also known as "A" line plants) and male-fertile in other cytoplasms (also known as "B" line plants), whereas the pollen-parent lines are not male sterile and do contain fertility restoring genes (also known as "R" line plants). The seed-parent lines are typically created to be cytoplasmically male sterile such that the anthers are minimal to non-existant in these plants thereby requiring cross-pollination. The seed-parent lines will only produce seed, and the cytoplasm is transmitted only through the egg. The pollen for cross pollination is furnished through the pollen-parent lines that contain the genes necessary for complete fertility restoration in the F1 hybrid, and the cross combines with the male sterile seed parent to produce a high-yielding single cross hybrid with good grain quality.

Typically, this cytoplasmic male sterility-fertility restorer system is performed for the production of hybrid seed by planting blocks of rows of male sterile (seed-parent) plants and blocks of rows of fertility restorer (pollen-parent) plants, such that the seed-parent plants are wind pollinated with pollen from the pollen-parent plant. This process produces a vigorous single-cross hybrid that is harvested and planted by the consumer. Male sterile, seed-parent plants can also be created by genetically breeding recessive male-sterile nuclear genes into a particular population, however the cytoplasmic male sterility-fertility restorer system is typically the system used for breeding hybrid *sorghum*. Sleper and Poehlman, 2006, Breeding Field Crops, Fifth Ed., Blackwell Publishing provides a good review of current *sorghum* breeding procedures and is incorporated herein in its entirety.

The present invention is not limited to the elite parent *sorghum* lines listed, and one skilled in the art will recognize that any elite *sorghum* line would be equally amenable to the compositions and methods as described herein.

Plant Transgenics

Heterologous genes intended for expression in plants are first assembled in expression vectors containing a heterologous gene and appropriate transcriptional and translational control elements, methods of which are well known to those skilled in the art. Methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., herein incorporated by reference).

In general, these vectors comprise a nucleic acid sequence encoding a heterologous gene operably linked to a promoter and other regulatory sequences (e.g., enhancers, polyadenylation signals, etc.) required for expression in a plant.

Promoters include, but are not limited to, constitutive promoters, tissue-, organ-, and developmentally specific promoters, and inducible promoters. Examples of promoters include, but are not limited to; constitutive promoter 35S of cauliflower mosaic virus; a wound-inducible promoter from tomato, leucine amino peptidase (Chao et al., 1999, Plant Physiol 120:979-992, herein incorporated by reference); a chemically-inducible promoter from tobacco, Pathogenesis-Related 1 (induced by salicylic acid and benzothiadiazole-7-carbothioic acid S-methyl ester); a heat shock promoter (U.S. Pat. No. 5,187,267, herein incorporated by reference); a tetracycline-inducible promoter (U.S. Pat. No. 5,057,422, herein incorporated by reference); and seed-specific promoters.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters such as those disclosed herein. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (Odell et al., 1985, Nature 313:810; Rosenberg et al., 1987, Gene, 56:125; Guerineau et al., 1991, Mol. Gen. Genet. 262:141; Proudfoot, 1991, Cell, 64:671; Sanfacon et al., 1990, Genes Dev. 5:141; Mogen et al., 1990, Plant Cell, 2:1261; Munroe et al., 1990, Gene, 91:151; Ballas et al., 1989, Nucleic Acids Res. 17:7891; Joshi et al., 1987, Nucleic Acid Res., 15:9627, all of which are incorporated herein by reference).

In some embodiments, constructs for expression of the heterologous gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. Intron sequences have been routinely incorporated into plant transformation vectors, typically within the non-translated leader.

In some embodiments, a construct for expression of the heterologous nucleic acid sequence of interest also includes a regulator such as a nuclear localization signal (Kalderon et al., 1984, Cell 39:499; Lassner et al., 1991, Plant Molecular Biology 17:229), a plant translational consensus sequence (Joshi, 1987, Nucleic Acids Research 15:6643), an intron (Luehrsen and Walbot, 1991, Mol. Gen. Genet. 225:81), and the like, operably linked to the nucleic acid sequence encoding an heterologous gene.

In preparing the construct comprising the nucleic acid sequence encoding an heterologous gene, or encoding a sequence designed to decrease heterologous gene expression, various DNA fragments can be manipulated so as to provide for the DNA sequences in the desired orientation (e.g., sense or antisense) and, as appropriate, in the desired reading frame. For example, adapters or linkers can be employed to join the DNA fragments, or other manipulations can be used to provide for convenient restriction sites, removal of superfluous DNA, removal of restriction sites, and the like. For this purpose, in vitro mutagenesis, primer repair, restriction, annealing, resection, ligation, and the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, 1982, Gene 19: 259; Bevan et al., 1983, Nature 304:184, all of which are incorporated herein by reference), the bar gene which confers resistance to the herbicide phosphinothricin (White et al., 1990. Nucl Acids Res. 18:1062; Spencer et al., 1990, Theor. Appl. Genet. 79:625, all of which are incorporated herein by reference), the hph gene which confers resistance to the antibiotic hygromycin (Blochlinger and Diggelmann, 1984, Mol. Cell. Biol. 4:2929, incorporated herein by reference), and the dhfr gene that confers resistance to methotrexate (Bourouis et al., 1983, EMBO J., 2:1099, incorporated herein by reference).

In some embodiments, the Ti (T-DNA) plasmid vector is adapted for use in an *Agrobacterium* mediated transfection process such as in U.S. Pat. No. 6,369,298 (*sorghum*), and U.S. Pat. Nos. 5,981,839, 6,051,757, 5,981,840, 5,824,877 and 4,940,838 all of which are incorporated by reference herein in their entireties. Construction of recombinant Ti and Ri plasmids in general follows methods typically used with more common vectors, such as pBR322. Additional use can be made of accessory genetic elements sometimes found with the native plasmids and sometimes constructed from foreign sequences. These may include, but are not limited to, structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Application Nos. WO 84/02913, 02919 and 02920; Herrera-Estrella, 1983, Nature 303:209-213; Fraley et al., 1983, Proc. Natl. Acad. Sci, USA 80:4803-4807; Horsch et al., 1984, Science 223:496-498; and DeBlock et al., 1984, EMBO J. 3:1681-1689, all of which are herein incorporated by reference.

The second system is called the "binary" system in which two plasmids are used and the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In some embodiments, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967 herein incorporated by reference). One of skill in the art knows that homologous recombination may be achieved using targeting vectors that contain sequences that are homologous to any part of the targeted plant gene, whether belonging to the regulatory elements of the gene or the coding regions of the gene. Homologous recombination may be achieved at any region of a plant gene so long as the nucleic acid sequence of regions flanking the site to be targeted is known. *Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

In some embodiments, the nucleic acids as disclosed herein are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or another promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments, a heterologous nucleic acid sequence of interest comprising a mutant ACC transgene, for example, as found in the germplasm designated KSU 06GH701-715bk or KSU 06GHATx623x714 deposited under ATCC accession Nos: PTA-8033 and PYA-8034, respectively, is introduced directly into a plant. In some embodiments, the transgene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714 (e.g., SEQ ID NO: 12). In some embodiments, the transgene is at least 70% homologous, at least 80% homologous, at least 85% homologous, at least 90% homologous, at least 95% homologous, at least 97% homologous, or at least 99% homologous to the ACC resistant herbicide gene as found in the germplasm KSU 06GH701-715bk or KSU 06GHATx623x714 comprising a tryptophan to cysteine amino acid substitution at an amino acid position aligning with $Trp_{7027}$ of the *A. myosuroides* Huds. ACC protein.

One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278, herein incorporated by reference).

Once a nucleic acid sequence encoding the heterologous gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method depends on the type of plant targeted for transformation. In some embodiments, the vector is maintained episomally. In some embodiments, the vector is integrated into the genome. In some embodiments, direct transformation in the plastid genome is used to introduce the vector into the plant cell (for example, see U.S. Pat. Nos. 5,451,513; 5,545,817; 5,545,818; PCT application WO 95/16783 all of which are incorporated herein by reference in their entireties).

The basic technique for chloroplast transformation involves introducing regions of cloned plastid DNA flanking a selectable marker together with the nucleic acid encoding the sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., 1990, Proc. Natl. Acad. Sci., 87:8526); Staub and Maliga, 1992, Plant Cell, 4:39, all of which are incorporated herein by reference). The presence of cloning sites between these markers allows creation of a plastid targeting vector introduction of foreign DNA molecules (Staub and Maliga, 1993, EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, 1993, Proc. Natl. Acad. Sci., 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of RNAs encoded by the DNA molecule.

In one embodiment, vectors useful in the practice of the present invention are microinjected directly into plant cells (Crossway, 1985, Mol. Gen. Genet, 202:179). In some embodiments, the vector is transferred into the plant cell by using polyethylene glycol (Krens et al., 1982, Nature, 296: 72; Crossway et al., 1986, BioTechniques, 4:320); fusion of protoplasts with other entities such as minicells, cells, lysosomes or other fusible lipid-surfaced bodies (Fraley et al., 1982, Proc. Natl. Acad. Sci., USA, 79:1859); and protoplast transformation (EP 0 292 435); direct gene transfer (Paszkowski et al., 1984, EMBO J., 3:2717; Hayashimoto et al., 1990, Plant Physiol. 93:857).

In some embodiments, the vector may also be introduced into the plant cells by electroporation. (Fromm, et al., 1985, Proc. Natl. Acad. Sci. USA 82:5824; Riggs et al., 1986, Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In addition to direct transformation, in some embodiments, the vectors comprising a nucleic acid sequence encoding a heterologous gene are transferred using *Agrobacterium*-mediated transformation (Hinchee et al., 1988, Biotechnology, 6:915; Ishida et al., 1996, Nature Biotechnology 14:745, all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introduced into appropriate plant cells, by means of the Ti plasmid of *Agrobacterium tumefaciens* (previously described). The Ti plasmid is transmitted to plant cells on infection by *Agrobacterium tumefaciens*, and is stably integrated into the plant genome (Schell, 1987, Science, 237: 1176). Species that are susceptible to infection by *Agrobacterium* may be transformed in vitro. Transformation methods for producing transgenic *sorghum* plants using *Agrobacterium*-mediated transformation are provided in U.S. Pat. No. 6,369,298.

In some embodiments, the vector is introduced through ballistic particle acceleration (U.S. Pat. No. 4,945,050; Casas et al., 1993, Proc. Natl. Acad. Sci. USA 90:11212, all references are incorporated herein in their entireties).

In some embodiments, after selecting for transformed plant material that can express a heterologous gene encoding a heterologous protein or variant thereof, whole plants are regenerated. Plant regeneration from cultured protoplasts is described in Evans et al., Handbook of Plant Cell Cultures, Vol. 1: (MacMillan Publishing Co. New York, (1983); Vasil I. R. (ed.), Cell Culture and Somatic Cell Genetics of Plants, Acad. Press, Orlando, Vol. I, (1984) and Vol. III, (1986), incorporated herein by reference in their entireties. It is known that many plants can be regenerated from cultured cells or tissues including, but not limited to, all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins Shoots and roots normally develop simultaneously. Efficient regeneration will depend on the medium, on the genotype, and on the history of the culture. The reproducibility of regeneration depends on the control of these variables.

The following examples are provided in order to demonstrate and further illustrate certain preferred embodiments and aspects of the present invention and are not to be construed as limiting the scope thereof.

EXAMPLES

Example 1

Herbicide Resistance in Wild *Sorghum* Genotype

Seeds of 83 wild *sorghum* populations from Bolivia were planted in a greenhouse for comparison with Tx2783, an herbicide susceptible elite *sorghum* genotype. Wild *sorghum* genotypes were planted in flats containing MetroMix 360 potting soil (Sun Gro) and greenhouse grown. Tx2783 was planted with the wild accessions in each flat for comparison. In one selection using clethodim, plants were sprayed with 0.09 lb ai clethodim acre$^{-1}$ at 18 days after planting. Tx2783 and many of the wild *sorghum*s died, but the herbicide tolerant entries were transplanted to pots for seed increase. In one selection using fluoazifop-P, flats with Tx2783 and wild accessions were sprayed with a rate of 0.12 lb ai fluazifop-P acre$^{-1}$ at 18 days after planting and with 0.36 lb ai fluazifop-P acre$^{-1}$ at 32 days after planting. Tx2783 and many of the wild *sorghum*s died, but the herbicide tolerant entries were transplanted to pots for seed increase. In a third experiment, plants were sprayed with a rate of 0.05 lb ai quizalofop acre$^{-1}$ at 18 days after planting and with 0.11 lb ai quizalofop acre$^{-1}$ at 32 days after planting. Tx2783 and many of the wild *sorghum*s died, but the herbicide tolerant entries were transplanted to pots for seed increase. One of the wild *sorghum* genotypes, Bol-71, expressed high levels of tolerance to each of the herbicides.

Example 2

Crosses of Bol-71 Wild *Sorghum* Genotype with Elite *Sorghum* Lines and Inheritance Determination Bol-71 was crossed with elite *sorghum* parent lines including Tx430, OOMN7645, BTx623, and ATx623. Seed set was excellent in every cross indicating that the wild genotype was sexually compatible with cultivated *sorghum* and could be used in a plant breeding program to produce herbicide tolerant *sorghum* varieties.

The mode of inheritance of herbicide tolerance was determined by planting seeds of Bol-71, F1 generation of cross ATx623×Bol-71, and Pioneer 84G62 (herbicide susceptible control) in flats containing MetroMix 360 potting soil in a greenhouse using a randomized complete block design (n=3). The plants were sprayed with 0.045 lb ai fluazifop-P acre$^{-1}$ at 14 days after planting. Pioneer 84G62 died between 12-16 days after spraying. The ATx623×Bol-71 and Bol-71 genotypes showed no herbicide damage, indicating that the herbicide tolerance trait was transmitted to cultivated *sorghum* and that herbicide tolerance was at least partially dominant in F1 hybrids.

Example 3

Gene Sequencing for ACC Resistance Gene

Gene sequencing efforts were initiated to determine if a genetic mutation might explain the herbicide tolerance phenotype. DNA was extracted from herbicide tolerant genotypes Bol-71 and R91 and herbicide susceptible genotypes Bol-36, ATx623, and Tx430. The polymerase chain reaction (PCR) using primers described by Délye and Michel (Weed Research, 2005, 45: 323-330; incorporated herein in its entirety) were used to amplify regions of the ACC gene associated with expression of herbicide tolerance. DNA sequencing (Kansas State University DNA sequencing facility) of resultant PCR products from herbicide tolerant and susceptible *sorghum* genotypes revealed that the susceptible genotypes contained the wild type sequence for the ACC gene as reported for *sorghum* (The Institute for Genomic Research (TIGR) Plant Transcript Assemblies database sequence designated TA3768_4558; incorporated herein in its entirety, see also table 1 below) and other cereal crops species; however, the herbicide tolerant genotypes contained a genetic mutation of TG<u>G</u> to TG<u>C</u> that results in a tryptophan to cysteine amino acid conversion at an amino acid position aligning with $Trp_{2027}$ of the *A. myosuroides* Huds. ACC protein (SEQ ID NO: 12) in the enzyme (FIG. 1; see Délye and Michel, Weed Research 2005 for amino acid numbering). This mutation is similar to the $Trp_{2027}Cys$ amino acid conversion in the ACC enzyme described in herbicide tolerant blackgrass (*Alopecurus myosuroides* Huds.) by Délye et al. (Plant Physiology 2005). The wild type *A. myosuroides* Huds. ACC protein (see Délye and Michel, Weed Research, 2005, 45:323-330; incorporated herein in its entirety) is represented by SEQ ID NO: 13. Blackgrass is a weed species and the only place in nature where this mutation has been reported, and the mutation has not been reported in *sorghum* or other crop species, or described as a target for developing herbicide tolerant crops.

TABLE 1

Sorghum ACC Carboxylase

Portion of the Wild Type Sorghum ACC Carboxylase
Gene Sequence
(SEQ ID NO: 1)
TGGCAGAGCAAANCTTGGAGGAATTCCTGTGGGTGTCATAGCTGTGGAGA

CACAGACCATGATGCAGCTTGTCCCTGCTGATCCAGGTCAGCTTGATTCC

CATGAGCGATCCGTTCCTCGGGCTGGACAAGTGTGGTTCCCAGATTCTGC

AACCAAGACAGCTCAGGCATTATTAGACTTCAACCGTGAAGGATTGCCTC

TGTTTATCCTGGCTAACTGGAGAGGTTT
                 ***
                [$Trp_{2031}$]

CTCTGGTGGACAGAGAGATCTCTTTGAAGGAATTCTTCAGGCTGGGTCAA

CAATTGTCGAGAACCTTAGGACATATAATCAGCCTGCGTTTGTCTACATT

CCTATGGCTGGAGAGCTTCGTGGAGGAGCTTGGGTTGTGGTCGATAGCAA

AATAAATCCAGACCGCATTGAGTGTTATGCTGAGAGGACTGCCAAAGGTA

TABLE 1-continued

Sorghum ACC Carboxylase

ATGTTCTCGAACCTCAAGGGTTAATTGAAATCAAGTTCAGGTCAGAGGAA

CTCCAAGACTGTATGGGTAGGCTTGACCCCGAGTTGATAAATCTGAAAGC

AAAACTCCAAGATGTAAAGCATGGAAATGGAAGTCTACCAGACATAGAAT

CCCTTCAGAAGAGTATAGAAGCACGTACGAAACAGTTGCTGCCTTTATAT

ACCCAGATTGCAATACGGTTTGCTGAATTGCATGATACTTCCCTAAGAAT

GGCAGCTAAAGGCGTGATTAAGAAAGTTGTAGACTGGGAAGAATCACGCT

CTTTCTTCTATAAAAGGCTACGGAGAAGGATCTCTGAAGATGTTCTTGCA

AAAGAAATAAGACATATAGTCGGTGACAACTTCACTCACCAATCAGCAAT

GGAGCTCATCAAGGAATGGTACCTGGCTTCTCCAGCCACAGCAGGAAGCA

CTGGATGGGATGACGATGATGCATTTGTTGCCTGGAAGGACAGTCCTGAA

AACTACAATGGATATATCCAAGAGCTAAGGGCTCAAAAAGTGTCTCAGTC

GCTCTCTGATCTCACTGACTCCAGTTCAGATCTACAAGCATTCTCGCAGG

GTCTTTCTACGCTATTAGATAAGATGGATCCCTCTCAAAGAGCGAAGTTT

GTTCAGGAAGTCAAGAAGGTCCTTGGTTGATGATATGATACCAACACATC

CAACACTATGTGCATGCTACATGTTTTTGTTCAAGTACATACATAGAAGG

ATATTGCTTGGCCTCGTTTGCTTGGCCGTTTGATCATGTCTGATCTAAGT

CGACCATTATTTGTTGAAACTTCCTTTTTGGACCTGGTGCTATGGTTGAT

GAATGTATATTGGACGTGTGCGACTGTGCGTTCTGCCAGGTGTAAGCTCA

AATGTTTAGACAGACCGAGTTATGGTTAGGAAGAGCACGAGTGAACATGT

TCTGGTTTTGCAGTGGTTCAGGAAGGCAGAAAGTTGTTTCACTGTAGTTC

TGAGATGTACTACCAGCGGCCCCCTGCTGTAATTTTAGGGTGTATAATGC

GGATACTAGTAAAACAATTGAGTGGTTCATTAAATTTTGAACTCGAATAA

TGTTTTTCTAGGCATATGTACCGTACCTCTACGTGAAATAAATGCTGTTG

AAATAGCATTCGACACCAGAATATATGTACCTTACCTAAGAGCTAAGTAT

TATAATACAACAAGTTGCTGGCCGTAAGATTTCTTT

Portion of the Sorghum ACC Carboxylase Gene
Sequence Encoding for $Trp_{2031}Cys$
(SEQ ID NO: 12)
TGGCAGAGCAAANCTTGGAGGAATTCCTGTGGGTGTCATAGCTGTGGAGA

CACAGACCATGATGCAGCTTGTCCCTGCTGATCCAGGTCAGCTTGATTCC

CATGAGCGATCCGTTCCTCGGGCTGGACAAGTGTGGTTCCCAGATTCTGC

AACCAAGACAGCTCAGGCATTATTAGACTTCAACCGTGAAGGATTGCCTC

TGTTTATCCTGGCTAACTGCAGAGGTTT
                 ***
                [$Trp_{2031}Cys$]

CTCTGGTGGACAGAGAGATCTCTTTGAAGGAATTCTTCAGGCTGGGTCAA

CAATTGTCGAGAACCTTAGGACATATAATCAGCCTGCGTTTGTCTACATT

CCTATGGCTGGAGAGCTTCGTGGAGGAGCTTGGGTTGTGGTCGATAGCAA

AATAAATCCAGACCGCATTGAGTGTTATGCTGAGAGGACTGCCAAAGGTA

ATGTTCTCGAACCTCAAGGGTTAATTGAAATCAAGTTCAGGTCAGAGGAA

CTCCAAGACTGTATGGGTAGGCTTGACCCCGAGTTGATAAATCTGAAAGC

AAAACTCCAAGATGTAAAGCATGGAAATGGAAGTCTACCAGACATAGAAT

TABLE 1-continued

Sorghum ACC Carboxylase

CCCTTCAGAAGAGTATAGAAGCACGTACGAAACAGTTGCTGCCTTTATAT

ACCCAGATTGCAATACGGTTTGCTGAATTGCATGATACTTCCCTAAGAAT

GGCAGCTAAAGGCGTGATTAAGAAAGTTGTAGACTGGGAAGAATCACGCT

CTTTCTTCTATAAAAGGCTACGGAGAAGGATCTCTGAAGATGTTCTTGCA

AAAGAAATAAGACATATAGTCGGTGACAACTTCACTCACCAATCAGCAAT

GGAGCTCATCAAGGAATGGTACCTGGCTTCTCCAGCCACAGCAGGAAGCA

CTGGATGGGATGACGATGATGCATTTGTTGCCTGGAAGGACAGTCCTGAA

AACTACAATGGATATATCCAAGAGCTAAGGGCTCAAAAAGTGTCTCAGTC

GCTCTCTGATCTCACTGACTCCAGTTCAGATCTACAAGCATTCTCGCAGG

GTCTTTCTACGCTATTAGATAAGATGGATCCCTCTCAAAGAGCGAAGTTT

GTTCAGGAAGTCAAGAAGGTCCTTGGTTGATGATATGATACCAACACATC

CAACACTATGTGCATGCTACATGTTTTTGTTCAAGTACATACATAGAAGG

ATATTGCTTGGCCTCGTTTGCTTGGCCGTTTGATCATGTCTGATCTAAGT

CGACCATTATTTGTTGAAACTTCCTTTTTGGACCTGGTGCTATGGTTGAT

GAATGTATATTGGACGTGTGCGACTGTGCGTTCTGCCAGGTGTAAGCTCA

TABLE 1-continued

Sorghum ACC Carboxylase

AATGTTTAGACAGACCGAGTTATGGTTAGGAAGAGCACGAGTGAACATGT

TCTGGTTTTGCAGTGGTTCAGGAAGGCAGAAAGTTGTTTCACTGTAGTTC

TGAGATGTACTACCAGCGGCCCCCTGCTGTAATTTTAGGGTGTATAATGC

GGATACTAGTAAAACAATTGAGTGGTTCATTAAATTTTGAACTCGAATAA

TGTTTTTCTAGGCATATGTACCGTACCTCTACGTGAAATAAATGCTGTTG

AAATAGCATTCGACACCAGAATATATGTACCTTACCTAAGAGCTAAGTAT

TATAATACAACAAGTTGCTGGCCGTAAGATTTCTTT

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A seed producing the germplasm of *sorghum* hybrid variety KSU 06 GHATx623x714, wherein representative seeds have been deposited under ATCC No. PYA-8034, and wherein:
   (i) said germplasm comprises a *sorghum* acetyl-CoA carboxylase gene comprising a 1664-base portion having a nucleotide sequence represented by SEQ ID NO: 12,
   (ii) said *sorghum* acetyl-CoA carboxylase gene encodes a *sorghum* acetyl-CoA protein having a tryptophan to cysteine amino acid substitution at an amino acid position aligning with $Trp_{2027}$ of SEQ ID NO: 13, and
   (iii) the expression of said *sorghum* acetyl-CoA carboxylase gene confers to said *sorghum* hybrid grown from said seed resistance to inhibition by one or more aryloxyphenoxypropionate acetyl-CoA carboxylase herbicides at levels of said one or more aryloxyphenoxypropionate herbicides that would normally inhibit the growth of a *sorghum* hybrid.

2. A method of controlling weeds in the vicinity of a cultivated *sorghum* hybrid, said method comprising:
   a) providing one or more acetyl-CoA carboxylase herbicides,
   b) applying said one or more acetyl-CoA carboxylase herbicides to a field comprising a *sorghum* hybrid plant grown from the seed of claim 1, and
   c) controlling weeds in the vicinity of said cultivated *sorghum* hybrid such that weed growth is adversely affected by the application of said one or more herbicides and growth of said cultivated *sorghum* hybrid is not adversely affected.

3. A method of producing an herbicide resistant *sorghum* plant, said method comprising crossing a *sorghum* hybrid plant grown from the seed of claim 1 with a different *sorghum* plant and selecting a progeny plant comprising SEQ ID NO: 12.

* * * * *

SEQUENCE LISTING

```
<160> NUMBER OF SEQ ID NOS: 13

<210> SEQ ID NO 1
<211> LENGTH: 1664
<212> TYPE: DNA
<213> ORGANISM: Sorghum bicolor
<220> FEATURE:
<221> NAME/KEY: misc_feature
<222> LOCATION: (13)..(13)
<223> OTHER INFORMATION: N = a, c, t or g

<400> SEQUENCE: 1
tggcagagca aacttggag gaattcctgt gggtgtcata gctgtggaga cacagaccat      60
gatgcagctt gtccctgctg atccaggtca gcttgattcc catgagcgat ccgttcctcg     120
ggctggacaa gtgtggttcc cagattctgc aaccaagaca gctcaggcat tattagactt    180
caaccgtgaa ggattgcctc tgtttatcct ggctaactgg agaggtttct ctggtggaca    240
gagagatctc tttgaaggaa ttcttcaggc tgggtcaaca attgtcgaga accttaggac    300
atataatcag cctgcgtttg tctacattcc tatggctgga gagcttcgtg gaggagcttg    360
ggttgtggtc gatagcaaaa taaatccaga ccgcattgag tgttatgctg agaggactgc    420
caaaggtaat gttctcgaac ctcaagggtt aattgaaatc aagttcaggt cagaggaact    480
ccaagactgt atgggtaggc ttgaccccga gttgataaat ctgaaagcaa aactccaaga    540
tgtaaagcat ggaaatggaa gtctaccaga catagaatcc cttcagaaga gtatagaagc    600
acgtacgaaa cagttgctgc ctttatatac ccagattgca atacggtttg ctgaattgca    660
tgatacttcc ctaagaatgg cagctaaagg cgtgattaag aaagttgtag actgggaaga    720
atcacgctct ttcttctata aaaggctacg gagaaggatc tctgaagatg ttcttgcaaa    780
agaaataaga catatagtcg gtgacaactt cactcaccaa tcagcaatgg agctcatcaa    840
```

```
ggaatggtac ctggcttctc cagccacagc aggaagcact ggatgggatg acgatgatgc    900
atttgttgcc tggaaggaca gtcctgaaaa ctacaatgga tatatccaag agctaagggc    960
tcaaaaagtg tctcagtcgc tctctgatct cactgactcc agttcagatc tacaagcatt   1020
ctcgcagggt ctttctacgc tattagataa gatggatccc tctcaaagag cgaagtttgt   1080
tcaggaagtc aagaaggtcc ttggttgatg atatgatacc aacacatcca acactatgtg   1140
catgctacat gttttgttc aagtacatac atagaaggat attgcttggc ctcgtttgct   1200
tggccgtttg atcatgtctg atctaagtcg accattattt gttgaaactt ccttttgga    1260
cctggtgcta tggttgatga atgtatattg gacgtgtgcg actgtgcgtt ctgccaggtg   1320
taagctcaaa tgtttagaca gaccgagtta tggttaggaa gagcacgagt gaacatgttc   1380
tggttttgca gtggtcagg aaggcagaaa gttgtttcac tgtagttctg agatgtacta    1440
ccagcggccc cctgctgtaa ttttagggtg tataatgcgg atactagtaa aacaattgag   1500
tggttcatta aattttgaac tcgaataatg tttttctagg catatgtacc gtacctctac   1560
gtgaaataaa tgctgttgaa atagcattcg acaccagaat atatgtacct tacctaagag   1620
ctaagtatta aatacaaca agttgctggc cgtaagattt cttt                     1664
```

```
<210> SEQ ID NO 2
<211> LENGTH: 41
<212> TYPE: DNA
<213> ORGANISM: Sorghum bicolor

<400> SEQUENCE: 2
ggctaactgc agaggtttct ctggtggaca gagagatctc t                        41

<210> SEQ ID NO 3
<211> LENGTH: 41
<212> TYPE: DNA
<213> ORGANISM: Sorghum bicolor

<400> SEQUENCE: 3
ggctaactgc agaggtttct ctggtggaca gagagatctc t                        41

<210> SEQ ID NO 4
<211> LENGTH: 41
<212> TYPE: DNA
<213> ORGANISM: Sorghum bicolor

<400> SEQUENCE: 4
ggctaactgg agaggtttct ctggtggaca gagagatctc t                        41

<210> SEQ ID NO 5
<211> LENGTH: 41
<212> TYPE: DNA
<213> ORGANISM: Sorghum bicolor

<400> SEQUENCE: 5
ggctaactgg agaggtttct ctggtggaca gagagatctc t                        41

<210> SEQ ID NO 6
<211> LENGTH: 41
<212> TYPE: DNA
<213> ORGANISM: Sorghum bicolor

<400> SEQUENCE: 6
ggctaactgg agaggtttct ctggtggaca gagagatctc t                        41
```

```
<210> SEQ ID NO 7
<211> LENGTH: 41
<212> TYPE: DNA
<213> ORGANISM: Sorghum bicolor

<400> SEQUENCE: 7
ggctaactgg agaggtttct ctggtggaca gagagatctc t                     41

<210> SEQ ID NO 8
<211> LENGTH: 41
<212> TYPE: DNA
<213> ORGANISM: Sorghum bicolor

<400> SEQUENCE: 8
ggctaactgc agaggtttct ctggtggaca gagagatctc t                     41

<210> SEQ ID NO 9
<211> LENGTH: 41
<212> TYPE: DNA
<213> ORGANISM: Sorghum bicolor

<400> SEQUENCE: 9
ggctaactgc agaggtttct ctggtggaca gagagatctc t                     41

<210> SEQ ID NO 10
<211> LENGTH: 41
<212> TYPE: DNA
<213> ORGANISM: Sorghum bicolor

<400> SEQUENCE: 10
ggctaactgc agaggtttct ctggtggaca gagagatctc t                     41

<210> SEQ ID NO 11
<211> LENGTH: 41
<212> TYPE: DNA
<213> ORGANISM: Sorghum bicolor

<400> SEQUENCE: 11
ggctaactgg agaggtttct ctggtggaca gagagatctc t                     41

<210> SEQ ID NO 12
<211> LENGTH: 1664
<212> TYPE: DNA
<213> ORGANISM: Sorghum bicolor
<220> FEATURE:
<221> NAME/KEY: misc_feature
<222> LOCATION: (13)..(13)
<223> OTHER INFORMATION: N = a, c, t or g

<400> SEQUENCE: 12
tggcagagca aancttggag gaattcctgt gggtgtcata gctgtggaga cacagaccat    60
gatgcagctt gtccctgctg atccaggtca gcttgattcc catgagcgat ccgttcctcg   120
ggctggacaa gtgtggttcc cagattctgc aaccaagaca gctcaggcat tattagactt   180
caaccgtgaa ggattgcctc tgtttatcct ggctaactgc agaggtttct ctggtggaca   240
gagagatctc tttgaaggaa ttcttcaggc tgggtcaaca attgtcgaga accttaggac   300
atataatcag cctgcgtttg tctacattcc tatggctgga gagcttcgtg gaggagcttg   360
ggttgtggtc gatagcaaaa taaatccaga ccgcattgag tgttatgctg agaggactgc   420
caaaggtaat gttctcgaac ctcaagggtt aattgaaatc aagttcaggt cagaggaact   480
ccaagactgt atgggtaggc ttgaccccga gttgataaat ctgaaagcaa aactccaaga   540
```

-continued

```
tgtaaagcat ggaaatggaa gtctaccaga catagaatcc cttcagaaga gtatagaagc    600
acgtacgaaa cagttgctgc ctttatatac ccagattgca atacggtttg ctgaattgca    660
tgatacttcc ctaagaatgg cagctaaagg cgtgattaag aaagttgtag actgggaaga    720
atcacgctct tcttctata aaaggctacg gagaaggatc tctgaagatg ttcttgcaaa     780
agaaataaga catatagtcg gtgacaactt cactcaccaa tcagcaatgg agctcatcaa    840
ggaatggtac ctggcttctc cagccacagc aggaagcact ggatgggatg acgatgatgc    900
atttgttgcc tggaaggaca gtcctgaaaa ctacaatgga tatatccaag agctaagggc    960
tcaaaaagtg tctcagtcgc tctctgatct cactgactcc agttcagatc tacaagcatt   1020
ctcgcagggt ctttctacgc tattagataa gatggatccc tctcaaagag cgaagtttgt   1080
tcaggaagtc aagaaggtcc ttggttgatg atatgatacc aacacatcca acactatgtg   1140
catgctacat gttttgttc aagtacatac atagaaggat attgcttggc ctcgtttgct    1200
tggccgtttg atcatgtctg atctaagtcg accattattt gttgaaactt ccttttgga    1260 cctggtgcta tggttgatga atgtatattg gacgtgtgcg actgtgcgtt ctgccaggtg    1320
taagctcaaa tgtttagaca gaccgagtta tggttaggaa gagcacgagt gaacatgttc    1380
tggttttgca gtggttcagg aaggcagaaa gttgtttcac tgtagttctg agatgtacta    1440
ccagcggccc cctgctgtaa ttttagggtg tataatgcgg atactagtaa aacaattgag    1500
tggttcatta aattttgaac tcgaataatg tttttctagg catatgtacc gtacctctac    1560
gtgaaataaa tgctgttgaa atagcattcg acaccagaat atatgtacct tacctaagag    1620
ctaagtatta taataacaaca agttgctggc cgtaagattt cttt                    1664
```

<210> SEQ ID NO 13
<211> LENGTH: 2320
<212> TYPE: PRT
<213> ORGANISM: Alopecurus myosuroides

<400> SEQUENCE: 13

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

-continued

```
Glu Asp Met Arg Ile Asn Ala Glu His Ile Arg Ile Ala Asp Gln Phe
            180                 185                 190
Val Glu Val Pro Gly Thr Asn Asn Asn Tyr Ala Asn Val Gln
        195                 200                 205
Leu Ile Val Glu Ile Ala Glu Arg Thr Gly Val Ser Ala Val Trp Pro
    210                 215                 220
Gly Trp Gly His Ala Ser Glu Asn Pro Glu Leu Pro Asp Ala Leu Thr
225                 230                 235                 240
Ala Lys Gly Ile Val Phe Leu Gly Pro Pro Ala Ser Ser Met Asn Ala
                245                 250                 255
Leu Gly Asp Lys Val Gly Ser Ala Leu Ile Ala Gln Ala Ala Gly Val
            260                 265                 270
Pro Thr Leu Ala Trp Ser Gly Ser His Val Glu Ile Pro Leu Glu Leu
        275                 280                 285
Cys Leu Asp Ser Ile Pro Glu Glu Met Tyr Arg Lys Ala Cys Val Thr
    290                 295                 300
Thr Ala Asp Glu Ala Val Ala Ser Cys Gln Met Ile Gly Tyr Pro Ala
305                 310                 315                 320
Met Ile Lys Ala Ser Trp Gly Gly Gly Gly Lys Gly Ile Arg Lys Val
                325                 330                 335
Asn Asn Asp Asp Glu Val Lys Ala Leu Phe Lys Gln Val Gln Gly Glu
            340                 345                 350
Val Pro Gly Ser Pro Ile Phe Ile Met Arg Leu Ala Ser Gln Ser Arg
        355                 360                 365
His Leu Glu Val Gln Leu Leu Cys Asp Glu Tyr Gly Asn Val Ala Ala
    370                 375                 380
Leu His Ser Arg Asp Cys Ser Val Gln Arg Arg His Gln Lys Ile Ile
385                 390                 395                 400
Glu Glu Gly Pro Val Thr Val Ala Pro Arg Glu Thr Val Lys Glu Leu
                405                 410                 415
Glu Gln Ala Ala Arg Arg Leu Ala Lys Ala Val Gly Tyr Val Gly Ala
            420                 425                 430
Ala Thr Val Glu Tyr Leu Tyr Ser Met Glu Thr Gly Glu Tyr Tyr Phe
        435                 440                 445
Leu Glu Leu Asn Pro Arg Leu Gln Val Glu His Pro Val Thr Glu Ser
    450                 455                 460
Ile Ala Glu Val Asn Leu Pro Ala Ala Gln Val Ala Val Gly Met Gly
465                 470                 475                 480
Ile Pro Leu Trp Gln Ile Pro Glu Ile Arg Arg Phe Tyr Gly Met Asp
                485                 490                 495
Asn Gly Gly Gly Tyr Asp Ile Trp Arg Lys Thr Ala Ala Leu Ala Thr
            500                 505                 510
Pro Phe Asn Phe Asp Glu Val Asp Ser Gln Trp Pro Lys Gly His Cys
        515                 520                 525
Val Ala Val Arg Ile Thr Ser Glu Asn Pro Asp Asp Gly Phe Lys Pro
    530                 535                 540
Thr Gly Gly Lys Val Lys Glu Ile Ser Phe Lys Ser Lys Pro Asn Val
545                 550                 555                 560
Trp Gly Tyr Phe Ser Val Lys Ser Gly Gly Gly Ile His Glu Phe Ala
                565                 570                 575
Asp Ser Gln Phe Gly His Val Phe Ala Tyr Gly Glu Thr Arg Ser Ala
            580                 585                 590
```

```
Ala Ile Thr Ser Met Ser Leu Ala Leu Lys Glu Ile Gln Ile Arg Gly
            595                 600                 605

Glu Ile His Thr Asn Val Asp Tyr Thr Val Asp Leu Leu Asn Ala Pro
610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
                660                 665                 670

Glu Tyr Val Ser Tyr Leu Ile Lys Gly Gln Ile Pro Pro Lys His Ile
            675                 680                 685

Ser Leu Val His Ser Thr Ile Ser Leu Asn Ile Glu Glu Ser Lys Tyr
690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
                740                 745                 750

Glu Ala Gly Gly Thr Arg Leu Leu Ile Asp Gly Lys Thr Cys Leu Leu
            755                 760                 765

Gln Asn Asp His Asp Pro Ser Arg Leu Leu Ala Glu Thr Pro Cys Lys
770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
                820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
                900                 905                 910

Leu Gln Trp Glu Glu Leu Met Ser Val Leu Ala Thr Arg Leu Pro Arg
            915                 920                 925

Arg Leu Lys Ser Glu Leu Glu Gly Lys Tyr Asn Glu Tyr Lys Leu Asn
930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His  Phe Ile Val Lys Ser  Leu Phe Glu
            995                 1000                1005
```

```
Glu Tyr Leu Ser Val Glu Glu Leu Phe Ser Asp Gly Ile Gln Ser
1010                1015                1020

Asp Val Ile Glu Arg Leu Arg Leu Gln Tyr Ser Lys Asp Leu Gln
1025                1030                1035

Lys Val Val Asp Ile Val Leu Ser His Gln Gly Val Arg Asn Lys
1040                1045                1050

Thr Lys Leu Ile Leu Ala Leu Met Glu Lys Leu Val Tyr Pro Asn
1055                1060                1065

Pro Ala Ala Tyr Arg Asp Gln Leu Ile Arg Phe Ser Ser Leu Asn
1070                1075                1080

His Lys Arg Tyr Tyr Lys Leu Ala Leu Lys Ala Ser Glu Leu Leu
1085                1090                1095

Glu Gln Thr Lys Leu Ser Glu Leu Arg Thr Ser Ile Ala Arg Asn
1100                1105                1110

Leu Ser Ala Leu Asp Met Phe Thr Glu Glu Lys Ala Asp Phe Ser
1115                1120                1125

Leu Gln Asp Arg Lys Leu Ala Ile Asn Glu Ser Met Gly Asp Leu
1130                1135                1140

Val Thr Ala Pro Leu Pro Val Glu Asp Ala Leu Val Ser Leu Phe
1145                1150                1155

Asp Cys Thr Asp Gln Thr Leu Gln Gln Arg Val Ile Gln Thr Tyr
1160                1165                1170

Ile Ser Arg Leu Tyr Gln Pro Gln Leu Val Lys Asp Ser Ile Gln
1175                1180                1185

Leu Lys Tyr Gln Asp Ser Gly Val Ile Ala Leu Trp Glu Phe Thr
1190                1195                1200

Glu Gly Asn His Glu Lys Arg Leu Gly Ala Met Val Ile Leu Lys
1205                1210                1215

Ser Leu Glu Ser Val Ser Thr Ala Ile Gly Ala Ala Leu Lys Asp
1220                1225                1230

Ala Ser His Tyr Ala Ser Ser Ala Gly Asn Thr Val His Ile Ala
1235                1240                1245

Leu Leu Asp Ala Asp Thr Gln Leu Asn Thr Thr Glu Asp Ser Gly
1250                1255                1260

Asp Asn Asp Gln Ala Gln Asp Lys Met Asp Lys Leu Ser Phe Val
1265                1270                1275

Leu Lys Gln Asp Val Val Met Ala Asp Leu Arg Ala Ala Asp Val
1280                1285                1290

Lys Val Val Ser Cys Ile Val Gln Arg Asp Gly Ala Ile Met Pro
1295                1300                1305

Met Arg Arg Thr Phe Leu Leu Ser Glu Glu Lys Leu Cys Tyr Glu
1310                1315                1320

Glu Glu Pro Ile Leu Arg His Val Glu Pro Leu Ser Ala Leu
1325                1330                1335

Leu Glu Leu Asp Lys Leu Lys Val Lys Gly Tyr Asn Glu Met Lys
1340                1345                1350

Tyr Thr Pro Ser Arg Asp Arg Gln Trp His Ile Tyr Thr Leu Arg
1355                1360                1365

Asn Thr Glu Asn Pro Lys Met Leu His Arg Val Phe Phe Arg Thr
1370                1375                1380

Leu Val Arg Gln Pro Ser Ala Gly Asn Arg Phe Thr Ser Asp His
1385                1390                1395
```

```
Ile Thr Asp Val Glu Val Gly His Ala Glu Pro Leu Ser Phe
1400             1405             1410

Thr Ser Ser Ser Ile Leu Lys Ser Leu Lys Ile Ala Lys Glu Glu
1415                 1420                 1425

Leu Glu Leu His Ala Ile Arg Thr Gly His Ser His Met Tyr Leu
1430                 1435                 1440

Cys Ile Leu Lys Glu Gln Lys Leu Leu Asp Leu Val Pro Val Ser
1445                 1450                 1455

Gly Asn Thr Val Val Asp Val Gly Gln Asp Glu Ala Thr Ala Cys
1460                 1465                 1470

Ser Leu Leu Lys Glu Met Ala Leu Lys Ile His Glu Leu Val Gly
1475                 1480                 1485

Ala Arg Met His His Leu Ser Val Cys Gln Trp Glu Val Lys Leu
1490                 1495                 1500

Lys Leu Val Ser Asp Gly Pro Ala Ser Gly Ser Trp Arg Val Val
1505                 1510                 1515

Thr Thr Asn Val Thr Gly His Thr Cys Thr Val Asp Ile Tyr Arg
1520                 1525                 1530

Glu Val Glu Asp Thr Glu Ser Gln Lys Leu Val Tyr His Ser Thr
1535                 1540                 1545

Ala Leu Ser Ser Gly Pro Leu His Gly Val Ala Leu Asn Thr Ser
1550                 1555                 1560

Tyr Gln Pro Leu Ser Val Ile Asp Leu Lys Arg Cys Ser Ala Arg
1565                 1570                 1575

Asn Asn Lys Thr Thr Tyr Cys Tyr Asp Phe Pro Leu Thr Phe Glu
1580                 1585                 1590

Ala Ala Val Gln Lys Ser Trp Ser Asn Ile Ser Ser Glu Asn Asn
1595                 1600                 1605

Gln Cys Tyr Val Lys Ala Thr Glu Leu Val Phe Ala Glu Lys Asn
1610                 1615                 1620

Gly Ser Trp Gly Thr Pro Ile Ile Pro Met Gln Arg Ala Ala Gly
1625                 1630                 1635

Leu Asn Asp Ile Gly Met Val Ala Trp Ile Leu Asp Met Ser Thr
1640                 1645                 1650

Pro Glu Phe Pro Ser Gly Arg Gln Ile Ile Val Ile Ala Asn Asp
1655                 1660                 1665

Ile Thr Phe Arg Ala Gly Ser Phe Gly Pro Arg Glu Asp Ala Phe
1670                 1675                 1680

Phe Glu Ala Val Thr Asn Leu Ala Cys Glu Lys Lys Leu Pro Leu
1685                 1690                 1695

Ile Tyr Leu Ala Ala Asn Ser Gly Ala Arg Ile Gly Ile Ala Asp
1700                 1705                 1710

Glu Val Lys Ser Cys Phe Arg Val Gly Trp Thr Asp Asp Ser Ser
1715                 1720                 1725

Pro Glu Arg Gly Phe Arg Tyr Ile Tyr Met Thr Asp Glu Asp His
1730                 1735                 1740

Asp Arg Ile Gly Ser Ser Val Ile Ala His Lys Met Gln Leu Asp
1745                 1750                 1755

Ser Gly Glu Ile Arg Trp Val Ile Asp Ser Val Val Gly Lys Glu
1760                 1765                 1770

Asp Gly Leu Gly Val Glu Asn Ile His Gly Ser Ala Ala Ile Ala
1775                 1780                 1785
```

-continued

```
Ser Ala Tyr Ser Arg Ala Tyr Glu Glu Thr Phe Thr Leu Thr Phe
    1790            1795                1800

Val Thr Gly Arg Thr Val Gly Ile Gly Ala Tyr Leu Ala Arg Leu
    1805            1810                1815

Gly Ile Arg Cys Ile Gln Arg Ile Asp Gln Pro Ile Ile Leu Thr
    1820            1825                1830

Gly Phe Ser Ala Leu Asn Lys Leu Leu Gly Arg Glu Val Tyr Ser
    1835            1840                1845

Ser His Met Gln Leu Gly Gly Pro Lys Ile Met Ala Thr Asn Gly
    1850            1855                1860

Val Val His Leu Thr Val Pro Asp Asp Leu Glu Gly Val Ser Asn
    1865            1870                1875

Ile Leu Arg Trp Leu Ser Tyr Val Pro Ala Asn Ile Gly Gly Pro
    1880            1885                1890

Leu Pro Ile Thr Lys Ser Leu Asp Pro Ile Asp Arg Pro Val Ala
    1895            1900                1905

Tyr Ile Pro Glu Asn Thr Cys Asp Pro Arg Ala Ala Ile Ser Gly
    1910            1915                1920

Ile Asp Asp Ser Gln Gly Lys Trp Leu Gly Gly Met Phe Asp Lys
    1925            1930                1935

Asp Ser Phe Val Glu Thr Phe Glu Gly Trp Ala Lys Thr Val Val
    1940            1945                1950

Thr Gly Arg Ala Lys Leu Gly Gly Ile Pro Val Gly Val Ile Ala
    1955            1960                1965

Val Glu Thr Gln Thr Met Met Gln Leu Val Pro Ala Asp Pro Gly
    1970            1975                1980

Gln Pro Asp Ser His Glu Arg Ser Val Pro Arg Ala Gly Gln Val
    1985            1990                1995

Trp Phe Pro Asp Ser Ala Thr Lys Thr Ala Gln Ala Met Leu Asp
    2000            2005                2010

Phe Asn Arg Glu Gly Leu Pro Leu Phe Ile Leu Ala Asn Trp Arg
    2015            2020                2025

Gly Phe Ser Gly Gly Gln Arg Asp Leu Phe Glu Gly Ile Leu Gln
    2030            2035                2040

Ala Gly Ser Thr Ile Val Glu Asn Leu Arg Thr Tyr Asn Gln Pro
    2045            2050                2055

Ala Phe Val Tyr Ile Pro Lys Ala Ala Glu Leu Arg Gly Gly Ala
    2060            2065                2070

Trp Val Val Ile Asp Ser Lys Ile Asn Pro Asp Arg Ile Glu Cys
    2075            2080                2085

Tyr Ala Glu Arg Thr Ala Lys Gly Asn Val Leu Glu Pro Gln Gly
    2090            2095                2100

Leu Ile Glu Ile Lys Phe Arg Ser Glu Glu Leu Lys Glu Cys Met
    2105            2110                2115

Gly Arg Leu Asp Pro Glu Leu Ile Asp Leu Lys Ala Arg Leu Gln
    2120            2125                2130

Gly Ala Asn Gly Ser Leu Ser Asp Gly Glu Ser Leu Gln Lys Ser
    2135            2140                2145

Ile Glu Ala Arg Lys Lys Gln Leu Leu Pro Leu Tyr Thr Gln Ile
    2150            2155                2160

Ala Val Arg Phe Ala Glu Leu His Asp Thr Ser Leu Arg Met Ala
    2165            2170                2175
```

-continued

```
Ala Lys Gly Val Ile Arg Lys Val Val Asp Trp Glu Asp Ser Arg
    2180            2185            2190

Ser Phe Phe Tyr Lys Arg Leu Arg Arg Arg Leu Ser Glu Asp Val
    2195            2200            2205

Leu Ala Lys Glu Ile Arg Gly Val Ile Gly Glu Lys Phe Pro His
    2210            2215            2220

Lys Ser Ala Ile Glu Leu Ile Lys Lys Trp Tyr Leu Ala Ser Glu
    2225            2230            2235

Ala Ala Ala Ala Gly Ser Thr Asp Trp Asp Asp Asp Ala Phe
    2240            2245            2250

Val Ala Trp Arg Glu Asn Pro Glu Asn Tyr Lys Glu Tyr Ile Lys
    2255            2260            2265

Glu Leu Arg Ala Gln Arg Val Ser Arg Leu Leu Ser Asp Val Ala
    2270            2275            2280

Gly Ser Ser Ser Asp Leu Gln Ala Leu Pro Gln Gly Leu Ser Met
    2285            2290            2295

Leu Leu Asp Lys Met Asp Pro Ser Lys Arg Ala Gln Phe Ile Glu
    2300            2305            2310

Glu Val Met Lys Val Leu Lys
    2315            2320
```